(12) United States Patent
Phillips et al.

(10) Patent No.: US 7,307,179 B2
(45) Date of Patent: Dec. 11, 2007

(54) PROCESS FOR PREPARING CYCLIC ORGANOHYDROGENSILOXANES

(75) Inventors: Robert N. Phillips, Cardiff (GB); Richard Gregory Taylor, Sully (GB)

(73) Assignee: Dow Corning Corporation, Midland, MI (US)

( * ) Notice: Subject to any disclaimer, the term of this patent is extended or adjusted under 35 U.S.C. 154(b) by 9 days.

(21) Appl. No.: 10/559,956

(22) PCT Filed: Jul. 2, 2004

(86) PCT No.: PCT/EP2004/007805

§ 371 (c)(1), (2), (4) Date: Mar. 9, 2006

(87) PCT Pub. No.: WO2005/005441

PCT Pub. Date: Jan. 20, 2005

(65) Prior Publication Data

US 2006/0173202 A1 Aug. 3, 2006

(30) Foreign Application Priority Data

Jul. 11, 2003 (GB) ................. 0316268.2

(51) Int. Cl.
*C07F 7/04* (2006.01)

(52) U.S. Cl. .................................... 556/451

(58) Field of Classification Search ........... 556/451
See application file for complete search history.

(56) References Cited

U.S. PATENT DOCUMENTS

| 5,196,559 A | 3/1993 | Schulz, Jr. et al. |
| 5,247,116 A | 9/1993 | Buese et al. |
| 5,395,956 A | 3/1995 | Haines et al. |
| 2002/0173613 A1* | 11/2002 | Tolentino et al. ............. 528/10 |

* cited by examiner

*Primary Examiner*—J. Parsa
(74) *Attorney, Agent, or Firm*—Matthew T. Fewkes; Roger E. Gobrogge

(57) ABSTRACT

A process for preparing cyclic organohydrogensiloxanes is disclosed. The process comprises the steps of (A) and (B). Step (A) comprising contacting a silane of the formula $RHSiCl_2$, where R is selected from alkyl radicals having 1 to 12 carbon atoms and aryl radicals, with water to form a hydrolyzate. The hydrolyzate formed in step (A) comprising cyclic organohydrogensiloxanes and linear organohydrogensiloxanes. Step (B) comprising contacting the hydrolyzate formed in (A) with an acidic rearrangement catalyst in the presence of an inert liquid diluent to increase the ratio of the cyclic organohydrogensiloxanes to linear organohydrogensiloxanes in the hydrolyzate. The process further characterized by that the acidic rearrangement catalyst is an organic compound containing a strong acid group which is dissolved in the inert diluent present.

7 Claims, 1 Drawing Sheet

PROCESS FOR PREPARING CYCLIC ORGANOHYDROGENSILOXANES

CROSS REFERENCE TO RELATED APPLICATIONS

This application is a U.S. national stage filing under 35 U.S.C. §371 of PCT Application No. PCT/EP2004/007805 filed on 2 Jul. 2004, currently pending, which claims the benefit of GB Patent Application No. 0316268.2 filed 11 Jul. 2003 under 35 U.S.C. §119 (a)-(d) and 35 U.S.C. §365(a). PCT Application No. PCT/EP2004/007805 and GB Patent Application No. 03162683.2 are hereby incorporated by reference.

BACKGROUND OF INVENTION

The present invention is a process for preparing cyclic organohydrogensiloxanes.

Cyclic organohydrogensiloxanes such as cyclic methylhydrogensiloxane are useful as crosslinkers in silicone coatings and encapsulating materials used in the electronic industry and in release paper coatings and can be used as intermediates to form SiH functional siloxanes. In typical processes for preparing organohydrogensiloxanes a first step involves the hydrolysis of an organohydrogendichlorosilane to form an equilibrium mixture containing cyclic organohydrogensiloxanes and short-chain linear organohydrogensiloxanes. Generally, the weight percent of cyclic organohydrogensiloxanes in the equilibrium mixture is small in relation to the weight percent of linear organohydrogensiloxanes present. Consequently when demand for cyclic organohydrogensiloxanes is high, an excess of linear organohydrogensiloxanes may be produced.

U.S. Pat. No. 5,395,956 describes a process comprising contacting an organohydrogendichlorosilane with about a stoichiometric equivalent of water to form a hydrolyzate, diluting the hydrolyzate in an inert solvent and contacting it with an acidic rearrangement catalyst to effect formation of cyclic organohydrogensiloxanes. The catalyst is generally a heterogeneous catalyst used as a fixed-bed or stirred-bed. U.S. Pat. No. 5,395,956 says that the acidic rearrangement catalyst can be a homogeneous catalyst such as hydrogen chloride, sulphuric acid, or chlorosulfonic acid, but that such homogeneous acids are generally not preferred since they must subsequently be neutralized.

U.S. Pat. No. 5,247,116 describes a process for producing cyclosiloxanes by contacting siloxanes with a strong acid catalyst in the absence of an added solvent.

SUMMARY OF INVENTION

A process according to the present invention for preparing cyclic organohydrogensiloxanes comprises (A) contacting a silane of the formula $RHSiCl_2$, where R is selected from alkyl radicals having 1 to 12 carbon atoms and aryl radicals, with water to form a hydrolyzate comprising cyclic organohydrogensiloxanes and linear organohydrogensiloxanes, and (B) contacting the hydrolyzate with an acidic rearrangement catalyst in the presence of an inert liquid diluent to increase the ratio of the cyclic organohydrogensiloxanes to linear organohydrogensiloxanes in the hydrolyzate, characterised in that the acidic rearrangement catalyst is an organic compound containing a strong acid group which is dissolved in the inert liquid diluent present.

The process of the invention is preferably carried out as a continuous process including the steps of:

(C) recovering the cyclic methylhydrogensiloxanes by separation from the linear methylhydrogensiloxanes and diluent, and (D) recycling the linear methylhydrogensiloxanes and diluent containing dissolved acidic rearrangement catalyst from Step (C) to Step (B).

The organic acidic rearrangement catalyst is thus continuously recycled through the rearrangement (B) and separation (C) steps with the inert diluent.

Figure 1:
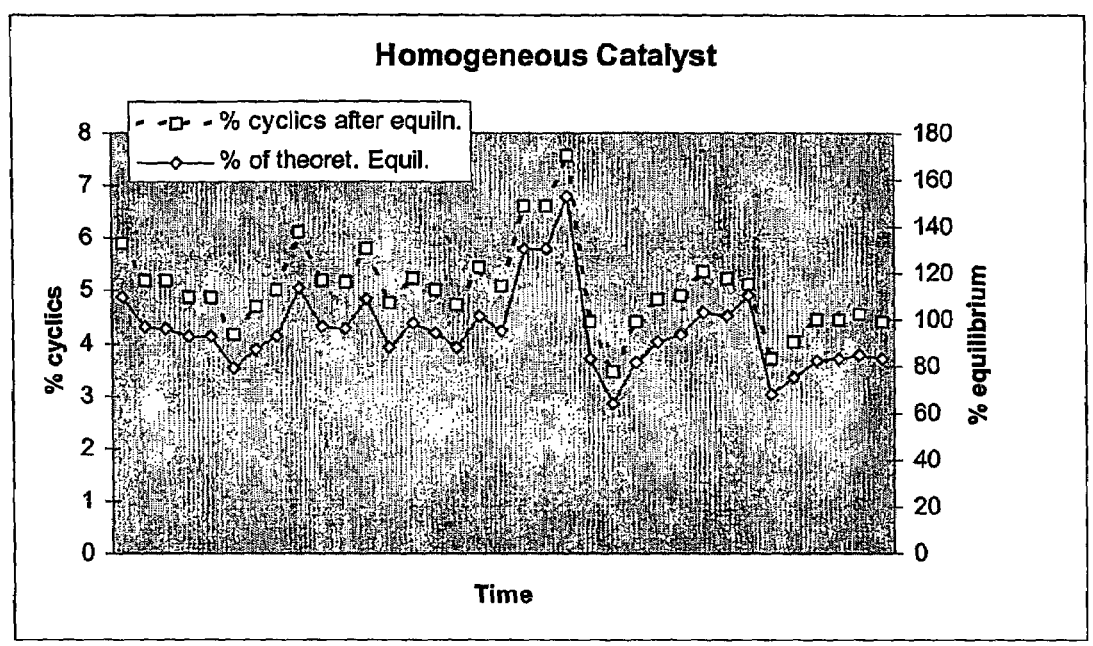
FIG. 1 is a graph of the results of Example 1 versus the % of theoretical equilibrium data.

We have found that when the process of U.S. Pat. No. 5,395,956 is operated using a fixed bed solid catalyst as described therein, equilibration to increase the ratio of the cyclic organohydrogensiloxanes to linear organohydrogensiloxanes in the hydrolyzate takes place initially, but the activity of the catalyst for this rearrangement fairly rapidly decreases over time. In the process of the present invention, the organic acid catalyst which is dissolved in the inert diluent retains its catalytic activity for increasing the ratio of the cyclic organohydrogensiloxanes to linear organohydrogensiloxanes in the hydrolyzate for a much longer time than the fixed bed solid catalyst.

DETAILED DESCRIPTION OF INVENTION

Silanes which can be hydrolyzed in the present process are described by formula (1). The silane may be a single species of silane as described by formula (1) or may be a mixture of such silanes. The silane contains substituent R, where R is selected from a group consisting of saturated monovalent hydrocarbon radicals comprising one to 12 carbon atoms and aryl radicals. R can be, for example, methyl, ethyl, propyl, isopropyl, butyl, tertiary butyl, sec-butyl, hexyl, cyclohexyl, dodecyl, phenyl, tolyl, and naphthyl. Preferred is when R is selected from a group consisting of methyl and phenyl. Most preferred is when R is methyl, i.e. methyldichlorosilane.

$$RHSiCl_2 \hspace{4cm} \text{Formula 1}$$

The silane is contacted with about a stoichiometric equivalent of water, where a stoichiometric equivalent of water is defined as 0.5 mole of water per mole of chlorine provided to the process by the silane. By use of the term "about" it is meant that the mole ratio of water to silane is within a range of plus or minus 20 percent of stoichiometric equivalence. Preferred is when the mole ratio of water to silane is within a range of −5% to +15%, more preferably from stoichiometric equivalence to an excess of 5 or 10% water.

Contact of the silane with water in step (A) can be conducted in standard reactors for hydrolyzing chlorosilanes. Although the pressure at which the process is conducted is not critical, it is preferred that the process be conducted at a pressure at which the silane is present as a liquid phase. Such pressure will be dependent upon the particular chlorosilane and the temperature at which the process is conducted. The hydrolysis process is preferably conducted at a temperature within a range from −15° C. to 120° C., more preferably 0° C. to 50° C., most preferably 20° C. to 40° C.

The hydrolyzate formed in the hydrolysis process is diluted in an inert liquid diluent, which may or may not be miscible with the hydrolyzate. By the term "inert" it is meant a diluent which does not otherwise have significant reaction in the process. Preferred liquid diluents are alkanes, including mixtures of alkanes. The alkanes can be linear or branched alkanes or a mixture thereof. The liquid diluent preferably has a boiling point above that of the cyclic hexamer of the organohydrogensiloxane. For example when the cyclic hexamer is methylhydrogensiloxane, suitable diluents are those alkanes having greater than about nine carbon atoms. One preferred diluent is the paraffin mixture of boiling point range 243° C. to 285° C. sold under the Trade Mark 'Isopar P'. Inert liquid diluents having a boiling point below that of the cyclic hexamer of the organohydrogensiloxane can also be used, but may make separation of the diluent from the cyclic organohydrogensiloxane more difficult.

The optimal weight ratio of hydrolyzate to diluent will depend upon such factors as the organic substituent substituted on the silicon atoms and the desired ratio of cyclic organohydrogensiloxane to linear organohydrogensiloxane in the rearranged hydrolyzate at equilibrium. Up to a certain maximum, the greater the dilution of the hydrolyzate the greater the ratio of the cyclic organohydrogensiloxanes to linear organohydrogensiloxanes in the rearranged hydrolyzate. The diluent preferably forms about 50 to 95% by weight of the liquid mixture of hydrolyzate and diluent, more preferably 60 to is 90%, most preferably 70 to 85%.

The diluted hydrolyzate is contacted with the organic acid rearrangement catalyst. It is generally preferred that the hydrolyzate is not contacted with the acidic rearrangement catalyst before being diluted. When the process of the invention is carried out as a continuous process including recycling of the linear methylhydrogensiloxanes and diluent containing dissolved acidic rearrangement catalyst, the diluent which contacts the hydrolyzate will contain the catalyst.

The acidic rearrangement catalyst is an organic compound containing a strong acid group which is dissolved in the inert liquid diluent present. By a strong acid group we mean that the organic acid has a pK of less than 3 and preferably less than 1.5. The acid is preferably a sulphonic acid but could alternatively be a phosphonic acid or an acid sulphate ester. Preferred sulphonic acids are aryl sulphonic acids, particularly alkylaryl sulphonic acids of the formula R'—Ar—SO$_3$H, where Ar is an aromatic nucleus such as a benzene or naphthalene nucleus and R' is an alkyl group which may have 1 to 30 carbon atoms but preferably has 8 to 20 carbon atoms, for example dodecylbenzenesulphonic acid. Alternative sulphonic acids which are suitable include alkyl sulphonic acids and halogenated aryl or alkyl sulphonic acids, for example trifluoromethane sulphonic acid.

The concentration of acidic rearrangement catalyst in the inert liquid diluent is preferably in the range 0.05 to 5% by weight, more preferably 0.07 to 0.2% by weight. In a continuous process, the concentration can be monitored as the linear methylhydrogensiloxanes and diluent containing dissolved acidic rearrangement catalyst is recycled from the separation step (C) to the rearrangement step (B), and can be adjusted by adding more catalyst or more diluent as required.

The temperature at which the rearrangement reaction is carried out is not critical and can generally be within a range of greater than about the freezing point of the inert diluent to about 150° C. Preferred is a temperature within a range of about 0° C. to 40° C., for example ambient temperature. The pressure at which the arrangement process is run is not critical and can be ambient pressure.

The vessel in which the rearrangement reaction is carried out can be any type of tank or reactor, for example a simple tank which optionally is stirred or a tube reactor. The reaction time can be from 1 minute to 24 hours or more; the rearrangement reaction is an equilibration reaction and equilibration is generally going on wherever the catalyst exists in contact with the siloxane and the solvent. Typical residence times of the catalyst, siloxane and solvent in a continuous process in which the catalyst is continuously recycled through the rearrangement and separation steps with the inert diluent are between 0.5 and 10 hours, particularly 1 to 5 hours. Since the rearrangement reaction is an equilibration reaction prolonged contact times are not harmful.

The cyclic organohydrogensiloxanes which can be recovered by the present process are described by formula (RHSiO)$_n$, where R is as previously described and n is an integer from three to about 12. The preferred organohydrogensiloxanes recovered from the present process are those where R is methyl and n is four, five, or six. The method for recovering the cyclic organohydrogensiloxanes from the present process is not critical and can be standard methods known in the art for separating cyclic siloxanes from mixtures. For example, the rearranged hydrolyzate can be flash distilled to separate the cyclic organohydrogensiloxanes from higher-boiling linear organohydrogensiloxanes and the bulk of the inert liquid diluent. The recovered higher-boiling linear organohydrogensiloxanes and diluent, and the catalyst dissolved therein, can be recycled to the rearrangement reactor. The recovered lower-boiling fraction containing the cyclic organohydrogensiloxanes can if desired be treated with additional water to effect polymerisation of low-boiling linear species to higher boiling linear species and facilitate their separation from the cyclic organohydrogensiloxanes. The resulting water phase can be removed by standard methods such as gravimetric or membrane separation. The cyclic organohydrogensiloxane-containing fraction can then be distilled to separate the cyclic organohydrogensiloxanes from higher-boiling linear species. The higher-boiling linear species can then be recycled to the rearrangement reactor for further processing.

The following Example, in which percentages are by weight, is provided to illustrate the present invention. The Example includes the single Figure of the accompanying drawings, which is a graph showing concentration of cyclic organohydrogensiloxanes in the mixture exiting the rearrangement reactor of Example 1 against time and also the yield of cyclic organohydrogensiloxanes in Example 1 against time expressed as % of the theoretical yield based on chlorosilane feed.

EXAMPLE 1

Methyldichlorosilane CH$_3$HSiCl$_2$ was mixed with a stoichiometric equivalent of water, i.e. 0.5 mole of water per mole of silicon bonded chlorine, in a steam heated continuous hydrolysis reactor. The hydrolysis reactor was maintained at 60 psig and the temperature of the reactor was controlled such that the hydrolyzate exiting the reactor was at a temperature of about 33° C. The hydrolyzate exiting the reactor was analysed by gas chromatography (GC) using a flame ionisation detector (FID) and found to comprise about 95 weight percent linear chlorine end-terminated methylhydrogensiloxane species and about five weight percent cyclic methylhydrogensiloxanes species. The hydrolyzate was diluted to about 20% in 'Isopar P' hydrocarbon solvent containing 0.1% dodecylbenzenesulphonic acid catalyst. Excess HCl gas from the hydrolysis reaction was collected for re-use.

The diluted hydrolyzate containing catalyst was fed through a simple rearrangement reactor tank at ambient temperature and pressure. Residence time of the diluted hydrolyzate in the reactor was about 3 hours. GC-FID analysis of the product exiting the rearrangement reactor showed the siloxane component to consist of about 70 weight percent linear chlorine end-terminated methylhydrogensiloxane species and about 30 weight percent cyclic methylhydrogensiloxane species.

The product from the rearrangement reactor was heated to drive off aqueous HCl, stripped in flash drums under vacuum and then vacuum distilled and the cyclic species and low-boiling linear species taken overhead. The bottom fraction was cooled and recycled to the rearrangement reactor.

Residual chlorine in the overhead fraction from the flash distillation (the crude product) was removed by contact with a calcium carbonate calcium chloride water system. The product was finally dried in a magnesium oxide bed. The recovered cyclic methylhydrogensiloxane fraction was analysed by GC-FID and found to comprise 99.7 weight percent cyclic methylhydrogensiloxanes of the tetramer, pentamer, and hexamer species. The process was run continuously for about 20 days.

The results are shown in FIG. 1. The % cyclics in the mixture exiting the rearrangement reactor was consistently above 4% and on average above 5%. The yield of cyclic methylhydrogensiloxanes was consistently above 80% of the theoretical yield based on chlorosilane feed, and on average about 100% of the theoretical yield. The % of theoretical equilibrium data is a comparison with an empirical relationship between siloxane and cyclics equilibrium concentration from lab experiments using a "standard" solid catalyst, Amberlyst(Trade Mark) sulphonated divinylbenzene styrene copolymer.

When the process of Example 1 was carried out using a fixed bed of solid catalyst in the rearrangement reactor, as described in U.S. Pat. No. 5,395,956, instead of adding dodecylbenzenesulphonic acid catalyst to the solvent, the % cyclics in the mixture exiting the rearrangement reactor was variable but usually in the range 1% to 3%.

The invention claimed is:

1. A process for preparing cyclic organohydrogensiloxanes comprising: (A) contacting a silane of the formula $RHSiCl_2$, where R is selected from alkyl radicals having 1 to 12 carbon atoms and aryl radicals, with water to form a hydrolyzate comprising cyclic organohydrogensiloxanes and linear organohydrogensiloxanes, and (B) contacting the hydrolyzate with an acidic rearrangement catalyst in the presence of an inert liquid diluent to increase the ratio of the cyclic organohydrogensiloxanes to linear organohydrogensiloxanes in the hydrolyzate, characterised in that the acidic rearrangement catalyst is an organic compound containing a strong acid group which is dissolved in the inert diluent present.

2. A process according to claim 1, characterised in that the acidic rearrangement catalyst is a sulfonic acid.

3. A process according to claim 2, characterised in that the sulfonic acid is an alkylaryl sulfonic acid.

4. A process according to claim 3, characterised in tat the sulfonic acid is dodecylbenzenesulfonic acid.

5. A process according to any of claims 1 to 4, characterised in that the process is a continuous process including the steps of (C) recovering the cyclic methylhydrogensiloxanes by separation from the linear methylhydrogensiloxanes and diluent, and (D) recycling the linear methylhydrogensiloxanes and diluent containing dissolved acidic rearrangement catalyst from Step (C) to Step (B).

6. A process according to any of claims 1 to 4, characterised in that the concentration of acidic rearrangement catalyst in the diluent is in the range 0.05 to 5% by weight.

7. A process according to claim 5, characterised in that the concentration of acidic rearrangement catalyst in the diluent is in the range 0.05 to 5% by weight.

* * * * *